US00PP34624P2

(12) United States Plant Patent
Zlesak

(10) Patent No.: US PP34,624 P2
(45) Date of Patent: Oct. 4, 2022

(54) ***PHYSOCARPUS* PLANT NAMED 'ZLENORA'**

(50) Latin Name: *Physocarpus opulifolius*
Varietal Denomination: ZLENora

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 0 days.

(21) Appl. No.: 17/803,370

(22) Filed: Jun. 2, 2022

(51) Int. Cl.
*A01H 5/02* (2018.01)
*A01H 6/74* (2018.01)

(52) U.S. Cl.
USPC ..... Plt./226
CPC ..... *A01H 6/74* (2018.05)

(58) Field of Classification Search
USPC ..... Plt./226
CPC ..... A01H 5/02
See application file for complete search history.

*Primary Examiner* — Kent L Bell

(57) ABSTRACT

'ZLENora' is a new and distinct cultivar of *Physocarpus opulifolius* plant having an upright, mounded, moderately dense plant habit; moderate overall plant size; moderate branching characteristics; medium sized yellow-green foliage; short to moderate internode length; resistance to powdery mildew; corymbs of blush-white flowers; light coral-pink follicle color in full sun for about a month after fertilization; and ability to root and grow vigorously from softwood and semi-hardwood stem cuttings.

6 Drawing Sheets

Latin name of genus and species: *Physocarpus opulifolius.*

Variety denomination: 'ZLENora'.

BACKGROUND OF THE INVENTION

The present invention relates to a new and distinct cultivar of *Physocarpus opulifolius* and will be referred to hereafter by its cultivar name, 'ZLENora'. *Physocarpus opulifolius* (commonly known as ninebark, common ninebark, Atlantic ninebark, and Eastern ninebark) is a deciduous shrub grown for landscape use. The key objective within the *Physocarpus opulifolius* breeding program I initiated in St. Paul, Minn. in 2001 and now continue in River Falls, Wisc. has been to develop new *Physocarpus opulifolius* cultivars that are compact growing, well-branched, healthy, and possess colorful foliage. One specific goal has been to produce a yellow-green leaved cultivar similar to *Physocarpus opulifolius* 'Dart's Gold' (not patented) but possessing more resistance to powdery mildew and having a more symmetric and full plant habit. 'ZLENora' meets this goal.

'ZLENora' originated as a unique seedling within an $F_2$ population that was developed by open-pollination of twelve $F_1$ seedlings (growing in isolation) of the cross of *Physocarpus opulifolius* 'Donna May' (disclosed in U.S. Plant Pat. No. 22,634) as the female parent and *Physocarpus opulifolius* 'Dart's Gold' (not patented) as the male parent. Ninebark displays self-incompatibility, and it is expected that the seeds that developed were from crosses between compatible full siblings. Seeds were harvested and bulked together from the $F_1$ siblings. Pollination that led to this $F_2$ population of seedlings from which 'ZLENora' was identified occurred in June 2014. The seeds of this population germinated during the winter of 2014/2015 indoors under florescent lights in St. Paul, Minn. 'ZLENora' stood out early on as a young seedling for having the brightest yellow-green foliage of all the new seedlings that season. After danger of frost was past, it was transitioned outdoors where it continued to be grown in a container. It was first asexually propagated using softwood cuttings its first summer (summer 2015). I have found that the characteristics of 'ZLENora' are stable and true to type over successive generations of vegetative propagation.

'ZLENora' is unique relative to other ninebark seedlings in my breeding program and all cultivars I am aware of because of its relatively bright yellow-green foliage, relatively strong powdery mildew resistance, and moderate overall plant and leaf size with improved plant density and symmetry for yellow-green leaved cultivars of similar overall plant size. 'ZLENora' first flowered in 2017. It has attractive blush-white flowers that are abundant and attractive against the colorful foliage. As follicles develop in full sun, they are a light coral-pink color for about a month and provide additional ornamental value. Vigorous current-season stems can naturally branch to a slight to moderate degree without pruning. The propensity for current season stems to branch leads to a naturally fuller and more symmetric plant habit than other moderate to larger sized cultivars on the market which typically possess stronger apical dominance and no to very limited current season branching without pruning.

SUMMARY OF THE INVENTION

The primary objective of the breeding goal was substantially achieved, along with other desirable improvements, as evidenced by the following unique combination of characteristics that are outstanding in the new variety and that distinguish it from other ninebark in my breeding program, as well as from all other cultivars of *Physocarpus opulifolius* of which I am aware:

1. Upright, mounded, moderately dense plant habit;
2. Moderate overall plant size;
3. Moderate branching characteristics;

4. Medium sized yellow-green foliage;
5. Short to moderate internode length;
6. Resistance to powdery mildew;
7. Corymbs of blush-white flowers;
8. Light coral-pink follicle color in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls, Wisc. and Cottage Grove, Minn. shows that the foregoing and all other characteristics and distinctions come true to form and are established and transmitted through succeeding asexual propagations.

Comparison with Parents

'ZLENora' was a seedling in the $F_2$ generation from a cross of 'Donna May' and 'Dart's Gold'. Compared to 'Dart's Gold' the plant habit of 'ZLENora' is a bit more dense and symmetrical without pruning and 'ZLENora' has displayed greater resistance to powdery mildew. 'ZLENora' and 'Dart's Gold' have similar foliage color and foliage size. Compared to 'Donna May', 'ZLENora' has an overall larger plant and foliage size. 'Donna May' has purple foliage, while 'ZLENora' has yellow-green foliage.

Comparison of 'ZLENora' with Similar Cultivars

The *Physocarpus opulifolius* cultivars with the greatest similarity to 'ZLENora' are 'Dart's Gold' and 'Podaras 3' (disclosed in U.S. Plant Pat. No. 22,362). Overall plant size and foliage color and size are similar between 'ZLENora' and 'Dart's Gold', but 'ZLENora' is slightly more dense and well-branched and has greater resistance to powdery mildew than 'Dart's Gold'. 'ZLENora' and 'Podaras 3' have similar resistance to powdery mildew and foliage size and color, but 'ZLENora' is more compact growing and well-branched than 'Podaras 3'.

BRIEF DESCRIPTION OF THE DRAWINGS

The accompanying colored photographs illustrate key features of 'ZLENora'. Photographs show the colors as true as it is reasonably possible to obtain with colored reproductions of this type. Colors in the photographs may differ slightly from the color values cited in the detailed botanical description, which accurately describe the colors of 'ZLENora'.

DETAILED BOTANICAL DESCRIPTION

Figure 1:
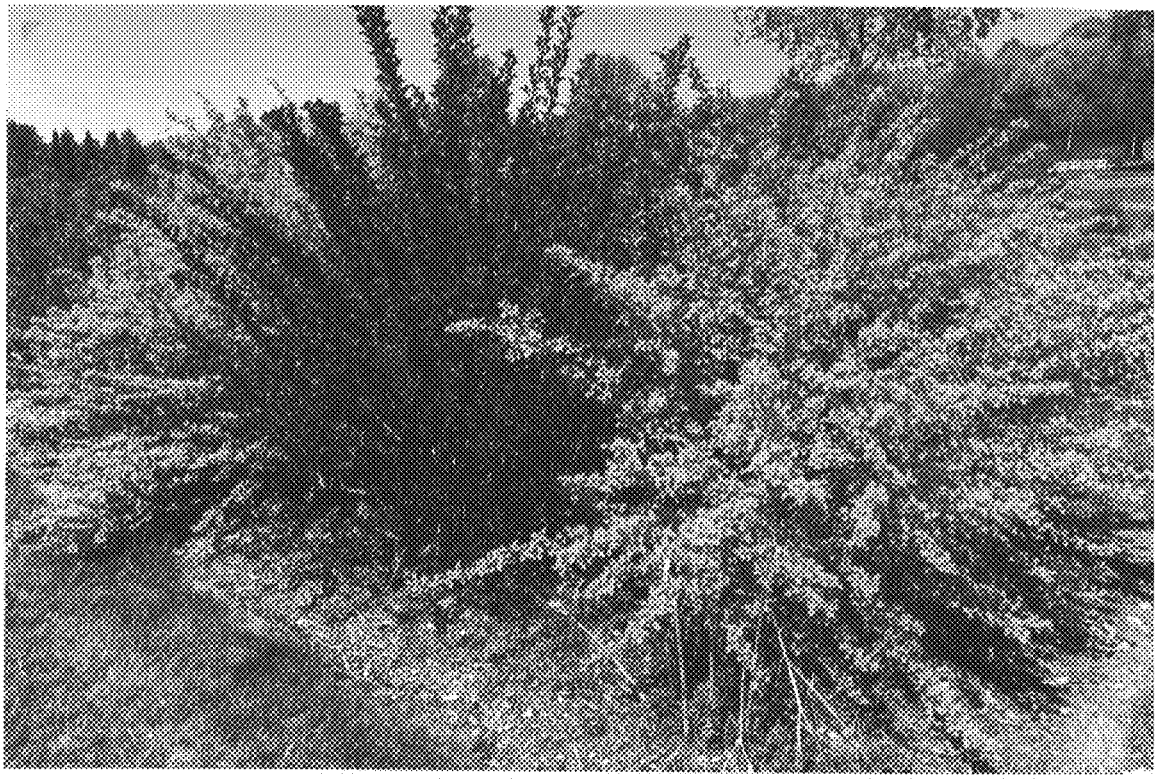
FIG. 1 illustrates a six-year-old unpruned plant of 'ZLENora' integrated in a landscape bed and leafing out in mid-May 2021. 'ZLENora' is the ninebark with yellow-green foliage on the right side of the bed in the photograph.
Figure 2:
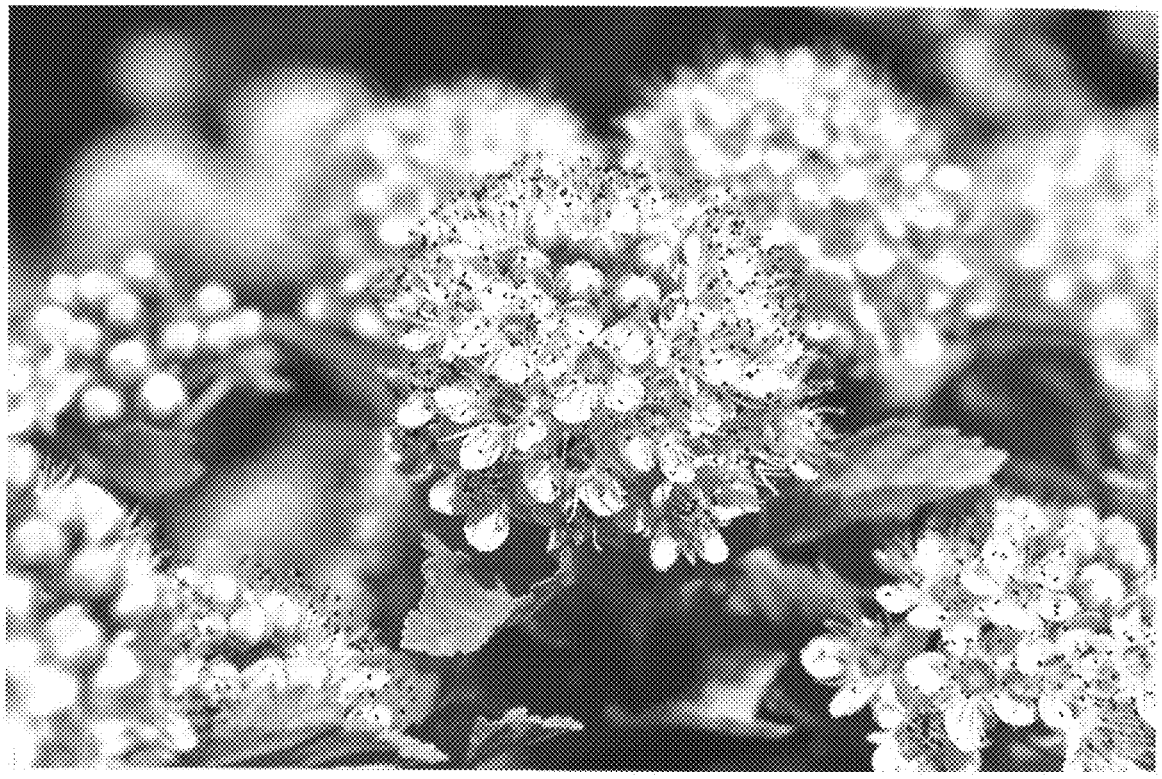
FIG. 2 illustrates corymbs of flowers of 'ZLENora' in mid-June 2021.
Figure 3:
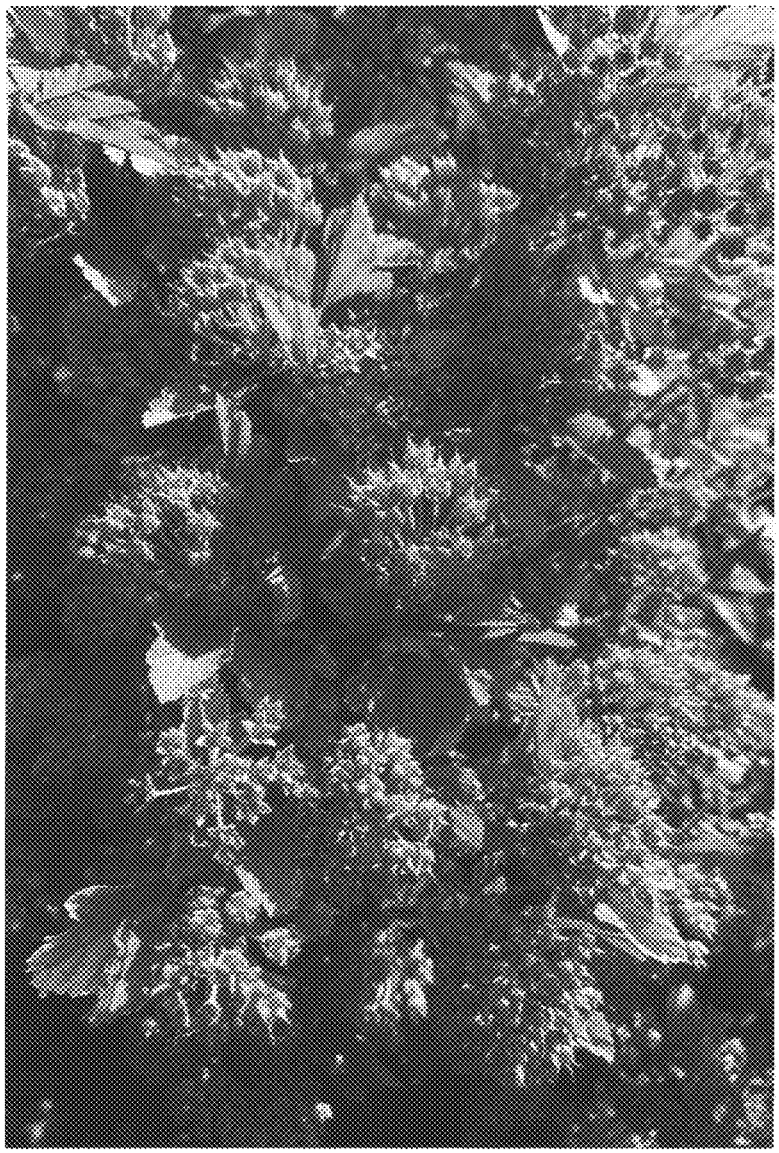
FIG. 3 illustrates developing follicles of 'ZLENora' in July 2021.
Figure 4:
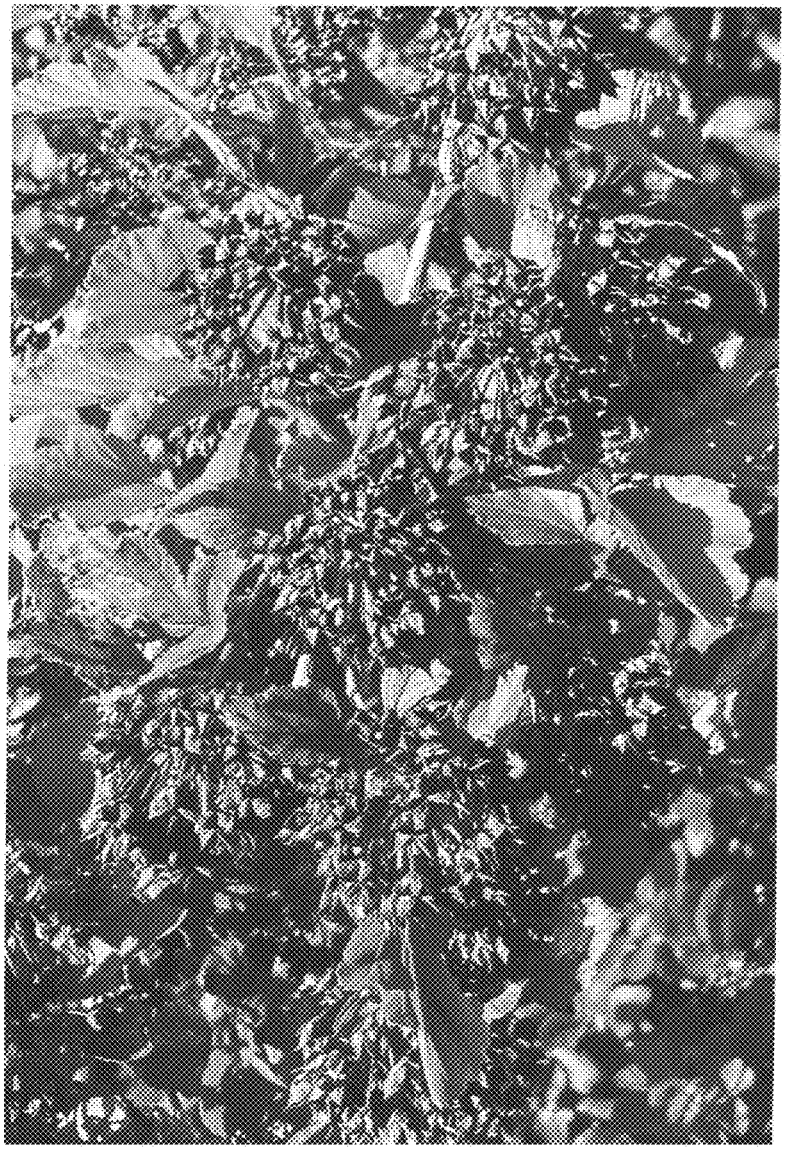
FIG. 4 illustrates maturing, dehiscing follicles of 'ZLENora' in October 2021.
Figure 5:
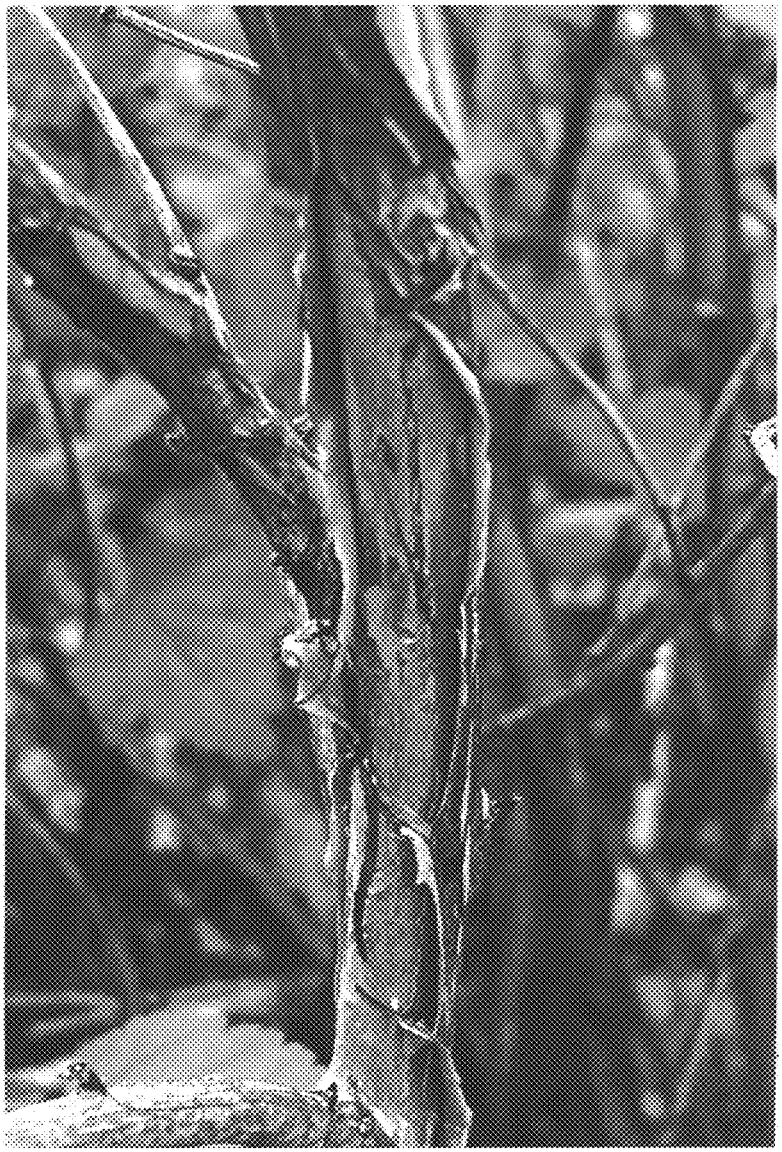
FIG. 5 illustrates stems at the base of a six-year-old plant of 'ZLENora' displaying exfoliating bark.
Figure 6:
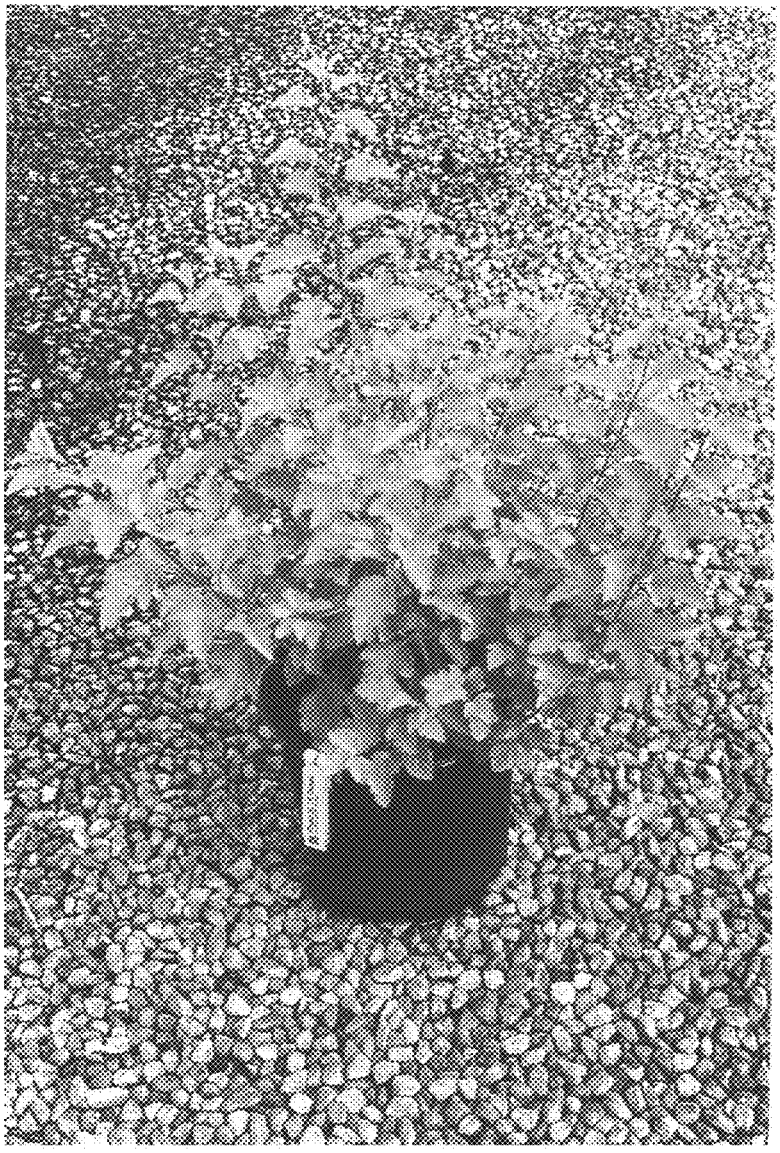
FIG. 6 illustrates a one-year-old plant of 'ZLENora' growing in a #2 nursery container July 2021.
Figure 7:
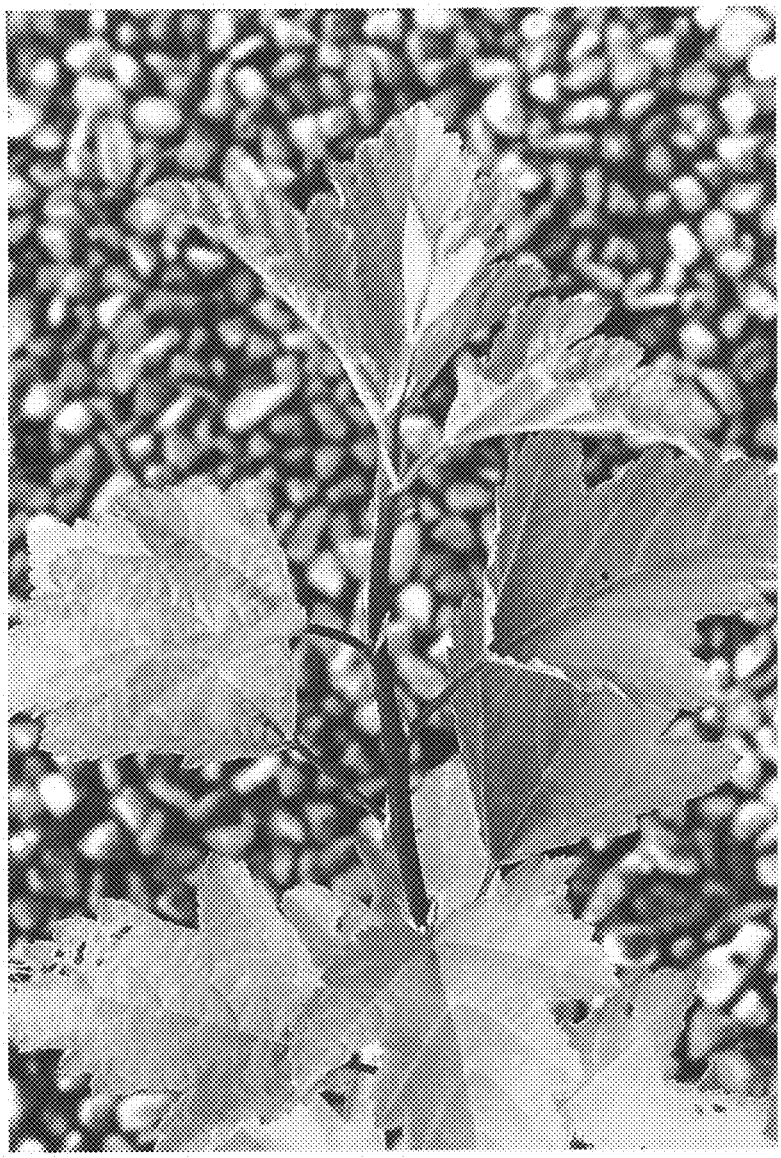
FIG. 7 illustrates a closeup of a current season stem of 'ZLENora' August 2021.

The following is a detailed description of 'ZLENora', the new *Physocarpus opulifolius* cultivar, with color descriptions using terminology in accordance with The Royal Horticultural Society (London) Colour Chart (2015), except where ordinary dictionary significance of color is indicated. The phenotype of the new cultivar may vary with variations in environmental, climatic, and cultural conditions, as it has not been tested under all possible environmental conditions. Descriptions are based on observations of a six-year-old plant growing in River Falls, Wisc. and one-year-old plants growing in Cottage Grove, Minn. during the 2021 growing season.

Classification:

*Botanical.*—*Physocarpus opulifolius* 'ZLENora'.

*Common names of the species.*—Ninebark, common ninebark, Atlantic ninebark, and Eastern ninebark.

*Commercial.*—Deciduous shrub.

Parentage:

*Origin.*—'ZLENora' is a seedling from within an $F_2$ population of a cross of *Physocarpus opulifolius* 'Donna May' and *Physocarpus opulifolius* 'Dart's Gold'.

General description:

*Plant habit.*—Upright, mounded, and moderately compact.

*Plant size.*—1.5-2.0 m in overall height and width.

*Growth habit.*—Vigorous and moderately dense with a moderate degree of branching.

*Blooming period.*—About 21 days from mid-June to early July.

*Hardiness.*—Cold hardy to at least USDA Zone 4.

*Root description.*—Fibrous and vigorous.

*Diseases and pest resistance.*—'ZLENora' has shown well above average resistance to powdery mildew, even with other ninebark genotypes infected with powdery mildew growing near it. There are multiple species of fungi that cause powdery mildew on ninebark, and it is unclear which species of fungi were infecting it and adjacent, more susceptible ninebark genotypes.

*Cultural requirements.*—'ZLENora' does well in full to partial sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in a greenhouse without supplemental lighting for cuttings to typically form visible roots.

*Time required to obtain a well-rooted cutting.*—It takes about 6 to 7 weeks to produce a well-rooted cutting in a 2-inch diameter container.

Branch description:

*Branch color.*—The color of current season stems is Yellow-Green Group 144D. The side of current season's stems in full sun has reddish highlights closest to Red-Purple Group 58A. The most mature stems on a six-year-old plant had a mixture of colors on the exfoliating bark; primarily Greyed-Yellow Group 161B and Greyed-Orange Group 177B, but there were also lighter colored areas close to Greyed-Yellow Group 161D and darker colored areas close to Greyed-Orange 165A.

*Branch size.*—Current season branches were approximately 12-60 cm in length and 1.5-4 mm in width.

The oldest branches on a six-year-old plant were up to 2.0 cm in diameter at the base of the plant.

*Branch surface.*—Young stems: Glabrous with a slight sheen. Older stems: Exfoliating bark layers are somewhat dull and no longer have a sheen.

*Internode length.*—1.0-3.0 cm.

*Branch habit.*—Vigorous current season's stems tend to produce a limited number of new stems from axillary buds without pruning. This leads to increased branching and a moderately dense plant.

Foliage description:

*Overall leaf size.*—Leaf length is 4.5-8.5 cm and leaf width is 2.5-6.0 cm.

*Leaf division.*—Simple.

*Leaf attachment.*—Petiolate.

*Leaf arrangement.*—Alternate.

*Leaf number.*—It varies, but a vigorously growing branch typically produces 30-60 leaves in a growing season.

*Leaf blade shape.*—Ovate in overall outline with three prominent lobes.

*Leaf blade base.*—Rounded.

*Leaf blade apex.*—Acute to cuneate.

*Leaf blade venation.*—Primary venation is palmate with three principal veins. The principal veins diverge at the juncture of the leaf blade and petiole and continue with one through the middle of each of the three lobes. Secondary venation off the three principal veins is pinnate.

*Leaf blade margin.*—The three primary lobes have secondary lobes or serrations. The margin on the three primary lobes is best described as doubly serrate. The serrations extend out from the edge of the main leaf blade about 1.0-1.5 mm and there is typically between 4-6 mm between the tips of primary serrations and 1-3 mm between the tips of secondary serrations.

*Leaf blade surface.*—Glabrous on upper and lower surfaces.

*Leaf blade size.*—The leaf blade is approximately 3.0-6.5 cm long and 2.5-6.0 cm wide.

*Leaf blade color.*—Young emerging leaf blades are Yellow-Green Group 153D on the upper and lower surfaces. Young expanded leaf blades are closest to Yellow-Green Group N144B on the upper surface and Yellow-Green Group 146D on the lower surface. Mature leaves are Yellow-Green Group 144A on the upper surface and Yellow-Green Group 146C on the lower surface. Where the sun especially hits the upper surface of the leaves, the color can be Yellow-Green Group N144A.

*Petiole size.*—About 1.0-2.0 cm in length and about 1 mm in width.

*Petiole shape.*—Sulcate. The petiole is generally round except for a longitudinal furrow running the length of the upper surface.

*Petiole color.*—Yellow-Green Group 146D.

*Petiole texture.*—Glabrous.

*Stipule number.*—There are two stipules at each node connected the stem with one on each side of the leaf petiole.

*Stipule size.*—2-3 mm long and 1.25 mm wide.

*Stipule shape.*—Generally lanceolate.

*Stipule color.*—Yellow-Green Group 146D on the upper and lower surfaces.

Flower description:

*Inflorescence type.*—A corymb with 20-30 rotate flowers arranged in an elongated hemisphere.

*Inflorescence size.*—Typically 2.0-2.5 cm in height and width.

*Inflorescence lastingness.*—The corymb has open flowers typically for up to 21 days with each individual flower open for approximately 3 days.

*Flower bud shape.*—Elliptic to oval.

*Flower bud size and proportions.*—3.0-4.0 mm in length and 3.0 mm in width. The receptacle of the bud accounts for about one half of the proximal end and the calyx accounts for about half of the distal end of an unopened flower bud.

*Flower bud color.*—The overall color of exposed petal undersides as the sepals open can best be described as White Group N155B. The sepals and receptacle are closest to Yellow-Green Group 144B.

*Flower size when fully open.*—7.0-10.0 mm in diameter and 4.0-5.0 mm in depth (not including pedicel).

*Flower symmetry.*—Actinomorphic.

*Flower fragrance.*—Slight and sweet.

*Petal number.*—5.

*Petal size.*—3.0-3.5 mm in length and width.

*Petal shape.*—Elliptic to obovate.

*Petal color.*—Expanding petals are White Group 155C on the upper and lower surfaces.

*Sepal number.*—5.

*Sepal size.*—Length is 2.0-3.0 mm and width is 1.5-2.0 mm.

*Sepal shape.*—Deltoid.

*Sepal color.*—Yellow-Green Group 145C on the upper surface and Yellow-Green Group 144B on the lower surface.

*Sepal texture.*—Hoary on both surfaces.

*Pedicel size.*—The length ranges from about 1.5 cm for the flowers coming from the proximal or lower end of the corymb to about 0.7 cm for the flowers nearest the terminal or center of the corymb. Pedicels are round in cross section and are about 1.0 mm in diameter.

*Pedicel color.*—Yellow-Green Group 144C.

*Pedicel and receptacle texture.*—Hoary.

*Subtending bract size.*—There is a subtending bract where each pedicel meets the peduncle of the corymb. The subtending bract is 2.0-3.0 mm long and 1 mm wide below the pedicels at the proximal end of the corymb to 1.25-1.5 mm long and 1.0 mm wide under the more distal pedicels at the terminal or top of the corymb.

*Subtending bract shape.*—Elliptic with 5-10 very small and irregularly spaced serrations that extend about 0.5-0.7 mm from the edge of the main margin.

*Subtending bract color.*—Yellow-Green Group 144C on both surfaces.

Gynoecium:

*Pistil number per flower.*—Typically there are 4, but sometimes 3.

*Stigma shape.*—Globular.

*Stigma size.*—0.25 mm in width and height.

*Stigma color.*—Yellow Green Group N144D.

*Style shape.*—Linear.

*Style size.*—About 4 mm long and 0.2 mm wide.

*Style color.*—White Group 155C.

*Ovary shape.*—Elliptic.

*Ovary size.*—About 0.5 mm in length and 0.3 mm in width.

*Ovary color.*—Yellow Green Group 146D with red highlights that are Red-Purple Group 61B.

Androecium:

*Stamen number per flower.*—Approximately 25.

*Anther shape.*—Elliptic to round.

*Anther size.*—0.4-0.5 mm in height and width.

*Anther color.*—Purple Group N77A.

*Pollen color.*—White Group 155C.

*Pollen abundance.*—Moderate.

*Filament shape.*—Linear.

*Filament size.*—2.0-4.0 mm long and 0.1-0.2 mm wide.

*Filament color.*—White Group 155C.

Fruit and seeds:

*Fruit.*—There are typically three or four firm-walled follicles that form per flower. Follicles can split along both sides of the seam, but split more readily along the inner or adaxial seam. Follicles are elongated and generally ovate in shape with acuminate tips. They are up to 8.0 mm long and approximately 2.0-3.0 mm wide at their widest point. After fertilization and expansion of successfully developing fruit, the follicle surface has a light coral-pink color in bright light close to Orange-Red Group 35B. Follicle color tends to be green when out of direct sunlight and near Yellow-Green Group 145C. As the follicles continue to mature, the coral-pink coloration dissipates. When mature and before turning brown, the color is Greyed-Yellow Group 161A. The final color when follicles dehisce is Brown Group 200C.

*Seeds per follicle.*—There are typically 1-2 seeds per follicle.

*Seed shape.*—Ovate.

*Seed size.*—Up to about 1.5 mm long and 1.25 mm wide.

*Seed color.*—Mature seed color as follicles open and seeds are exposed and dehisce is closest to Greyed-Orange Group 164B.

Winter hardiness: Acclimated plants of 'ZLENora' in Cottage Grove, Minn. and River Falls, Wisc. have displayed strong stem survival (complete survival to very minor tip dieback) in United States Department of Agriculture cold hardiness zone 4 without insulation.

I claim:

1. A new and distinct cultivar of *Physocarpus opulifolius* plant named 'ZLENora' substantially as herein shown and described, characterized particularly by its upright, mounded, moderately dense plant habit; moderate overall plant size; moderate branching characteristics; medium sized yellow-green foliage; short to moderate internode length; resistance to powdery mildew; corymbs of blush-white flowers; light coral-pink follicle color in full sun for about a month after fertilization; and ability to root and grow vigorously from softwood and semi-hardwood stem cuttings.

* * * * *